(12) United States Patent
Yoneya et al.

(10) Patent No.: US 6,487,368 B1
(45) Date of Patent: Nov. 26, 2002

(54) FUNDUS PHOTOGRAPHING DEVICE

(75) Inventors: Shin Yoneya, Maebashi (JP); Tsuguo Nanjo, Toyohashi (JP)

(73) Assignee: Nidek Co., Ltd., Gamagori (JP)

( * ) Notice: Subject to any disclaimer, the term of this patent is extended or adjusted under 35 U.S.C. 154(b) by 0 days.

(21) Appl. No.: 09/727,701

(22) Filed: Dec. 4, 2000

(30) Foreign Application Priority Data

Sep. 12, 1999 (JP) ............................................. 11-349908

(51) Int. Cl.[7] .............................. A61B 3/14; G03B 29/00
(52) U.S. Cl. ......................... 396/18; 351/206; 351/211; 351/213
(58) Field of Search .................... 396/18, 159; 351/206, 351/207, 210, 211, 213, 221; 600/431, 318

(56) References Cited

U.S. PATENT DOCUMENTS

| 5,247,318 A | 9/1993 | Suzuki |
| 5,400,791 A | 3/1995 | Schlier et al. |
| 5,557,349 A | 9/1996 | Yoneya et al. |
| 6,270,749 B1 * | 8/2001 | Blumenkranz et al. ...... 424/9.6 |

FOREIGN PATENT DOCUMENTS

| JP | 6-114009 | 4/1994 |
| JP | 9-28676 | 2/1997 |
| JP | 10-43139 | 2/1998 |
| JP | 2802356 | 7/1998 |
| JP | 11-197114 | 7/1999 |
| JP | 11-225972 | 8/1999 |

* cited by examiner

Primary Examiner—D. Rutledge
(74) Attorney, Agent, or Firm—Oliff & Berridge, PLC (57) ABSTRACT

A fundus photographing device for conducting infrared fluorescence photography on a fundus of an examinee's eye after intravenously injecting a fluorescent agent which emits fluorescence of an infrared region into veins is disclosed. This device includes an illumination optical system 1 for illuminating the fundus with exciting light, thereby exciting the injected fluorescent agent, the exciting light being of wavelengths in a wavelength region of not maximum absorption but maximum fluorescent intensity of the fluorescent agent.

7 Claims, 9 Drawing Sheets

| TIME | EXCITATION WAVELENGTH | MAXIMUM FLUORESCENCE WAVELENGTH | FLUORESCENT INTENSITY (*) |
|---|---|---|---|
| 30 sec. | 735nm | 838nm | 34.3 (100.0) |
| | 780nm | 838nm | 10.3 ( 29.2) |
| | 790nm | 828nm | 14.7 ( 42.8) |
| 60 sec. | 735nm | 836nm | 39.2 (114.3) |
| | 780nm | 830nm | 14.5 ( 42.2) |
| | 790nm | 826nm | 19.6 ( 57.1) |
| 2 min. | 735nm | 832nm | 38.6 (112.5) |
| | 780nm | 828nm | 15.2 ( 44.3) |
| | 790nm | 832nm | 20.4 ( 59.4) |
| 3 min. | 735nm | 833nm | 36.0 (104.9) |
| | 780nm | 825nm | 12.7 ( 37.0) |
| | 790nm | 825nm | 18.9 ( 55.1) |
| 6 min. | 735nm | 827nm | 28.5 ( 83.0) |
| | 780nm | 822nm | 12.0 ( 34.9) |
| | 790nm | 825nm | 17.3 ( 50.4) |

*PARENTHESES( ) INDICATE RELATIVE FLUORESCENT INTENSITY WITH REFERENCE TO EXCITATION WAVELENGTH OF 735nm FOR 30 sec.

FUNDUS PHOTOGRAPHING DEVICE

BACKGROUND OF THE INVENTION

1. Field of the Invention

The present invention relates to a fundus photographing device to be used in ophthalmology clinics, and particularly to a fundus photographing device for fluorescent photography with infrared light.

2. Description of Related Art

There has been known a fundus photographing device for photographing an image of a fundus with infrared fluorescence emitted from choroidal veins of an examinee's eye. For the photography, indocyanine green (hereinafter referred to as ICG) which is a fluorescent agent is intravenously injected at first into the choroidal veins. The fundus of the examinee's eye is then illuminated with infrared light to excite the ICG circulated in the fundus (the choroidal veins). Thus the image of the fundus is photographed by the fundus photographing device with the infrared fluorescence emitted from the choroidal veins.

ICG has a peak absorption wavelength in a range of about 780 nm to 805 nm. In the infrared fluorescence photography using ICG, generally, the fundus is illuminated with exciting light through an exciter filter capable of sufficiently transmitting light of wavelengths of above 780 nm, while cutting light of wavelengths of about 800 nm or more. On the other hand, the ICG circulated in the fundus (the choroidal veins) and excited by the exciting light will emit fluorescence with a peak of about 830 nm. To prevent false fluorescence resulting from the exciting light from being mixed in a fluorescence photograph, the photography is carried out through a barrier filter capable of filtering fluorescence to allow transmission of the fluorescence having long wavelengths of about 820 nm or more.

Instead of the device using the exciter filter, there has recently been proposed a photographing device using, as an exciting light source, a laser diode which is a light source that emits light of a single wavelength having a peak of about 790 nm.

However, the infrared fluorescence of ICG emitted from the fundus (the choroidal veins) is very faint, which is about $\frac{1}{25}$ to $\frac{1}{50}$ in fluorescent intensity as compared with the fluorescence in a visible fluorescence photography using fluorescein as a fluorescent agent. Thus, the conventional device could only photograph the eye fundus with fluorescence of very low luminance. Therefore, thee are tendencies that only the sites where blood vessels lie on top of one another or plural blood vessels gather can be observed. In particular, the fluorescence at the early stage of ICG injection into the choroidal veins could hardly be captured. As a result, there were many insufficiencies in observation and photography of the choroidal circulation dynamics.

SUMMARY OF THE INVENTION

The present invention has been made in view of the above circumstances and has an object to overcome the above problems and to provide a fundus photographing device capable of efficiently photographing the fundus of an examinee's eye with infrared fluorescence of high luminance, thereby providing more detailed information for diagnosis of choroidal circulation dynamics of the examinee's eye.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a fundus photographing device for conducting infrared fluorescence photography on a fundus of an examinee's eye after intravenously injecting a fluorescent agent which emits fluorescence of an infrared region into veins, the device including: an illumination optical system for illuminating the fundus with exciting light, thereby exciting the injected fluorescent agent, the exciting light being of wavelengths in a wavelength region of not maximum absorption but maximum fluorescent intensity of the fluorescent agent.

According to another aspect of the present invention, there is provided a fundus photographing device for conducting infrared fluorescence photography on a fundus of an examinee's eye after intravenously injecting a fluorescent agent which emits fluorescence of an infrared region into veins, the device including: an illumination optical system for illuminating the fundus with exciting light, thereby exciting the injected fluorescent agent, the exciting light being of wavelengths with a peak in a range of approximately 725 nm to 745 nm; and a photographing optical system including filtering means for filtering infrared fluorescence from the injected fluorescent agent and a photographing element for photographing an image of the fundus with the infrared fluorescence filtered through the filtering means.

Moreover, according to another aspect of the present invention, there is provided a fundus photographing device for conducting infrared fluorescence photography on a fundus of an examinee's eye after intravenously injecting a fluorescent agent which emits fluorescence of an infrared region into veins, the device including: an illumination optical system for illuminating the fundus with exciting light of wavelengths in a predetermined wavelength region, thereby exciting the injected fluorescent agent; and a photographing optical system including a barrier filter for filtering infrared fluorescence from the injected fluorescent agent and a photographing element for photographing an image of the fundus with the infrared fluorescence filtered through the barrier filter, the barrier filter having a property of transmitting wavelengths in a predetermined wavelength region different from the wavelength region of the exciting light.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

A detailed description of a preferred embodiment of a fundus photographing device embodying the present invention will now be given referring to the accompanying drawings.

At first, explanation will be made on wavelengths of exciting light and wavelengths of fluorescence for ICG fluorescence photography.

As mentioned above, ICG has the maximum absorption wavelength in a range of about 680 nm to 805 nm. When injected into blood and excited by exciting light, the ICG will emit fluorescence with the peak wavelength of about 830 nm. In the conventional ICG fluorescence photography, the wavelengths of the exciting light and the property of a barrier filter provided in the photographing side have been determined based on the above properties. However, applicants reviewed and examined as to whether the use of the exciting light of wavelengths in the range of about 780 nm to 805 nm really could provide the best excitation efficiency.

When human serum samples containing ICG are excited by whichever wavelengths of the exciting light, the fluorescence shows the maximum fluorescent intensity when the fluorescence wavelength is about 830 nm. It is therefore conceivable that, when the fluorescent intensity of the fluorescence wavelengths of about 830 nm is measured while shifting the wavelength of the exciting light, the excitation wavelength whereby the maximum fluorescent intensity is obtained corresponds to the wavelength of the exciting light capable of providing the best excitation efficiency. Hence, the fluorescent intensity with respect to the fluorescence wavelengths of about 830 nm were measured with a monochromator, a photoelectric multiplier or the like with respect to a human serum sample containing ICG poured into a triangular cell on condition that the wavelength of the exciting light was selectively shifted in a range of about 660 nm to 810 nm. Measurement results thereon are shown as an excitation spectrum in FIG. 1.

Figure 1:
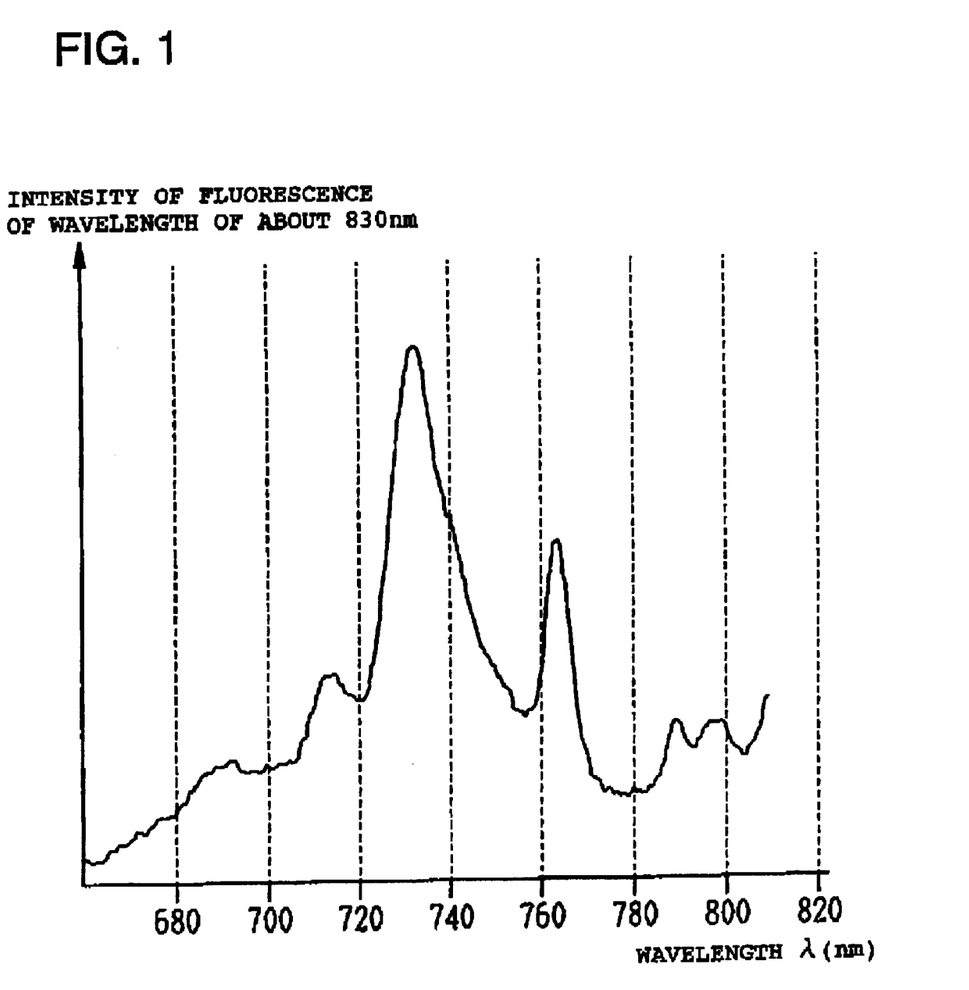
FIG. 1 is a graph showing an excitation spectrum obtained by measurements of fluorescent intensity of wavelength of about 830 nm of ICG injected into human serum.

As seen in the excitation spectrum in FIG. 1, the fluorescent intensity of wavelengths of about 830 nm became the maximum when the ICG was exited by the exciting light of wavelengths of about 732–735 nm, and the second intensity was obtained with respect to about 762–766 nm. The fluorescent intensity resulting from the exciting light of wavelengths of about 780–805 nm was low. This indicates that, in the infrared fluorescence photography using ICG, the use of the exciting light having its center wavelength of about 735 nm is more effective than that with wavelengths of about 780–805 nm which correspond to the maximum absorption wavelength of ICG.

In general, the maximum fluorescent intensity is obtained when a fluorescent agent is excited by exciting light of wavelengths close to the maximum absorption wavelength in an absorption spectrum. One example of the fluorescent agent is fluorescein used in the visible fluorescence photography.

Figure 7:
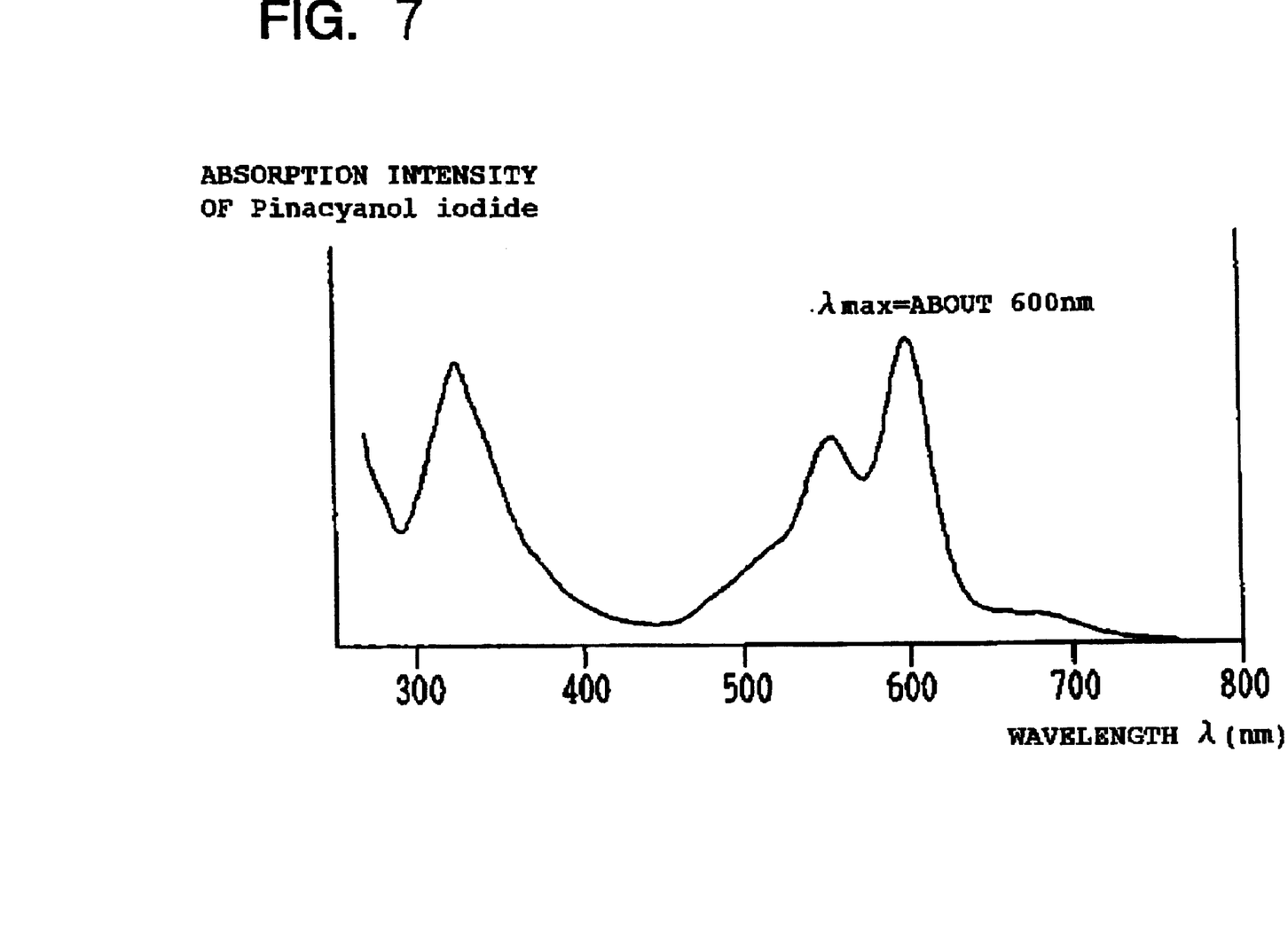
FIG. 7 is a graph showing an absorption spectrum of Pinacyanol iodide which is a cyanine base dye.
Figure 8:
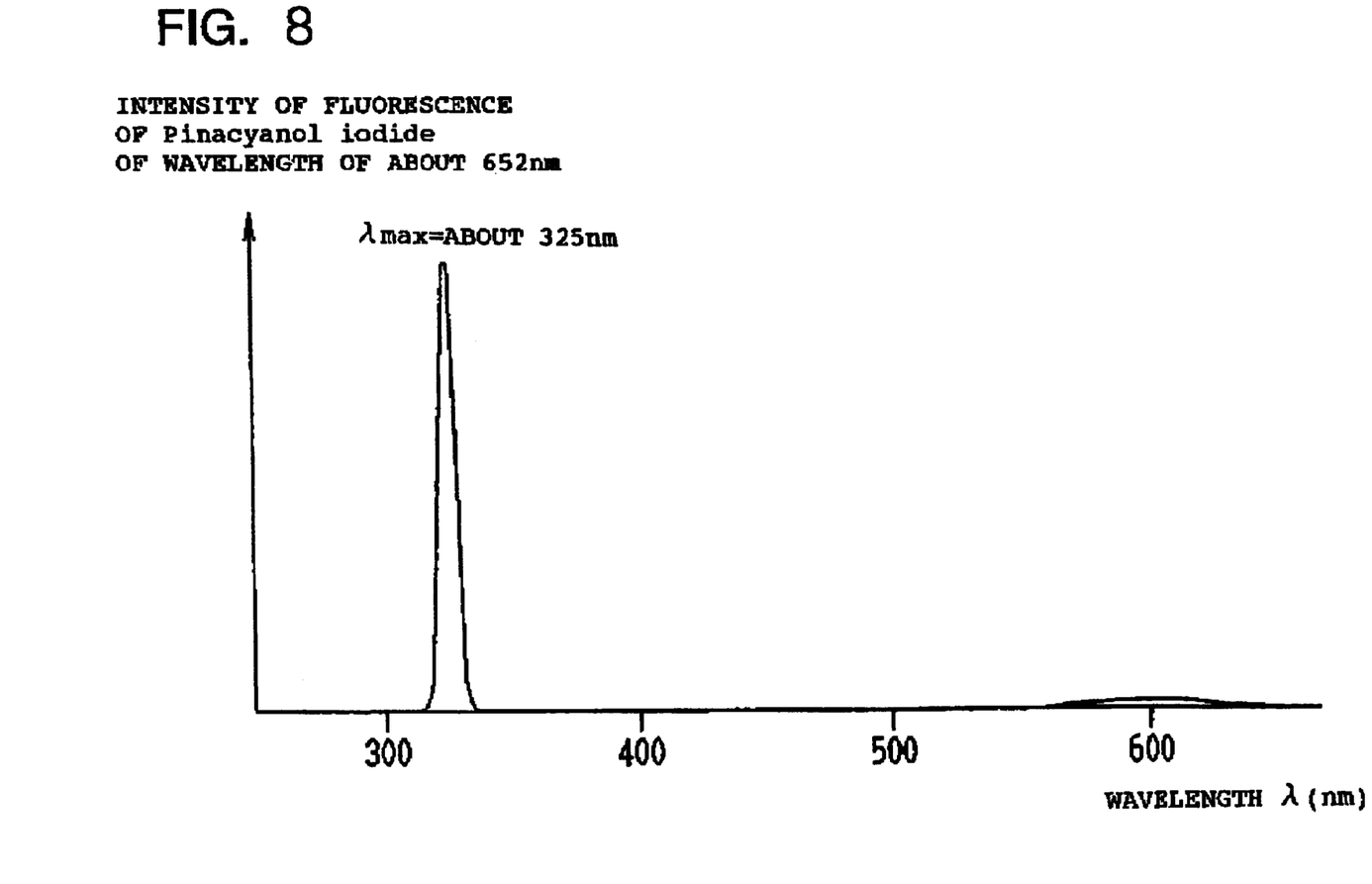
FIG. 8 is a graph showing an excitation spectrum of Pinacyanol iodide of a fluorescence wavelength of about 625 nm.
Figure 9:
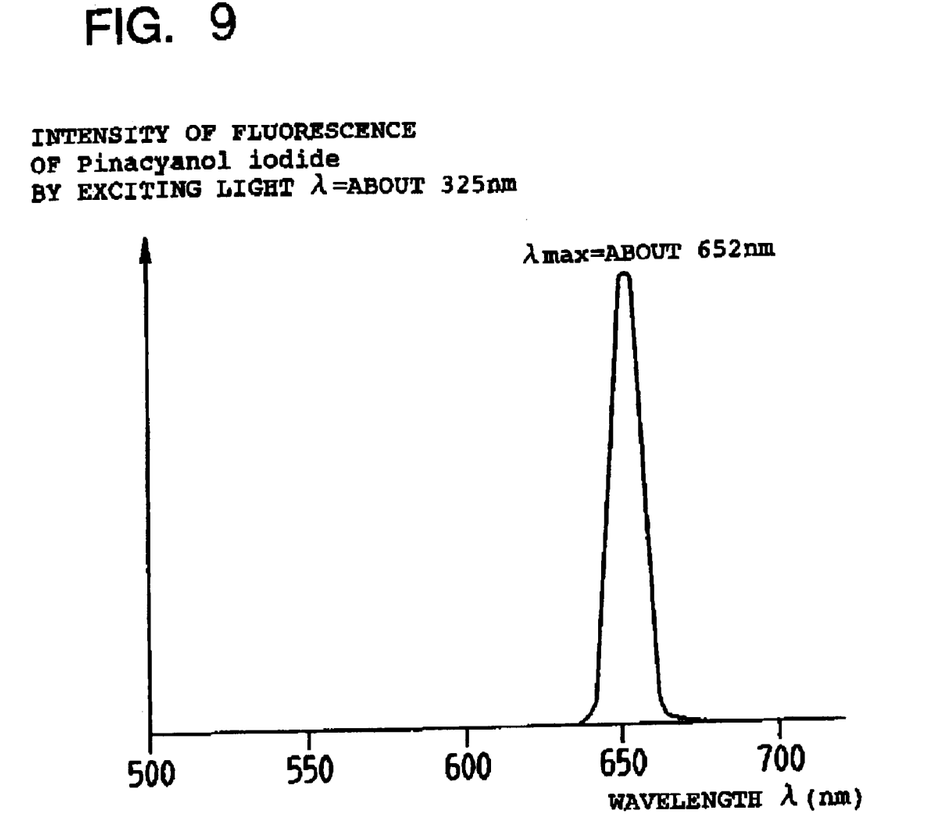
FIG. 9 is a graph showing a fluorescence spectrum of Pinacyanol iodide on condition that the exciting light is of a wavelength of about 325 nm.

On the other hand, measurement results on Pinacyanol iodide which is a cyanine base dye, like ICG, are as follows. As seen from the absorption spectrum in FIG. 7, the maximum absorption wavelength of the dye was about 600 nm on condition that the dye was dissolved in an aqueous solution. Measuring an excitation spectrum, however, as shown in FIG. 8, the maximum excitation wavelength was about 325 nm close to the maximum absorption wavelength in a near-ultraviolet region of the dye, then the dye showed the fluorescence spectrum with the maximum fluorescent intensity wavelength of about 625 nm (see FIG. 9). Although the dye was excited by the exciting light of a wavelength of about 600 nm which was the maximum absorption wavelength of the dye, the fluorescence of about 652 nm was extremely weak. This demonstrates that the maximum excitation wavelength with respect to the cyanine base dye did not always correspond to the maximum absorption wavelength.

Figure 2:
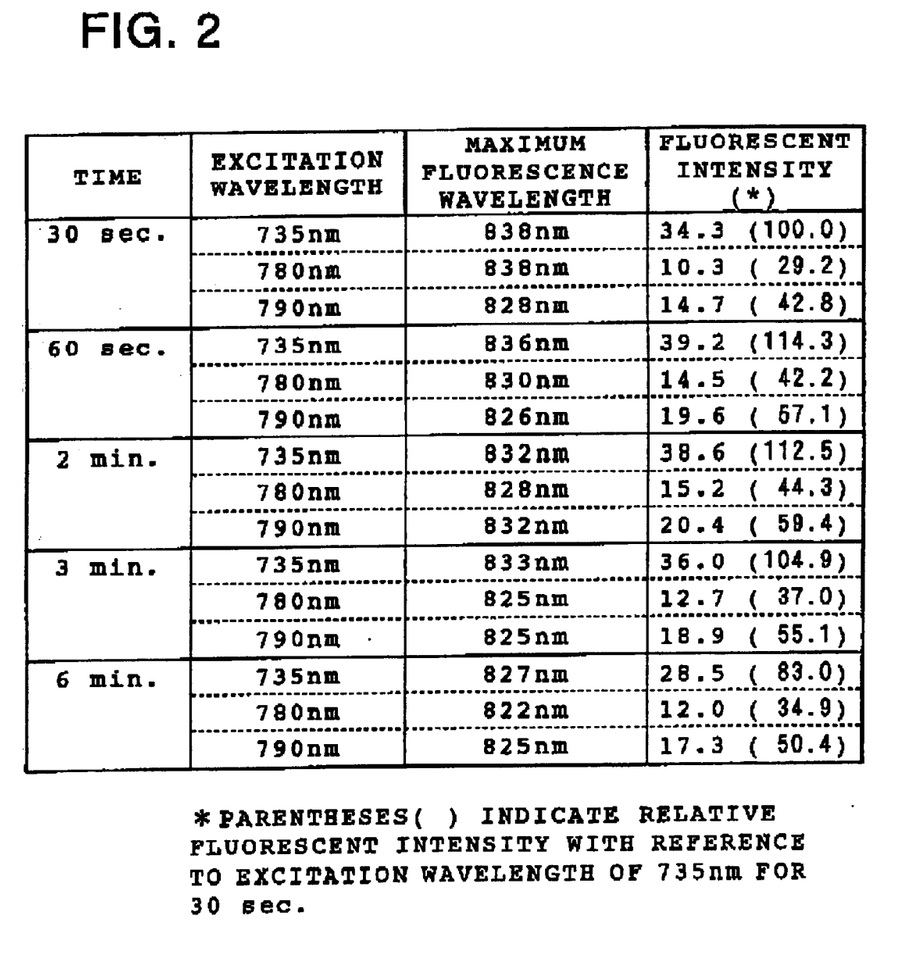
FIG. 2 is a table showing measurement results on maximum fluorescence wavelengths and respective fluorescent intensity on condition that a wavelength of exciting light is set to 735 nm, 780 nm, and 790 nm respectively.

Next, measurements were made on the maximum wavelengths of fluorescence and respective fluorescent intensity on condition that the exciting light was set to be of wavelengths of 735 nm, 780 nm, and 690 nm respectively. The measurements were conducted at 30 sec., 60 sec., 2 min., 3 min., and 5 min. after injection of ICG into a blood sample. FIG. 2 shows the results of those measurements. For any of the excitation wavelengths, the maximum fluorescence wavelength was in a range of 820 to 840 nm. There were not seen remarkable differences among the maximum fluorescence wavelengths due to the difference in excitation wavelength. On the other hand, the fluorescent intensity was the highest when the excitation wavelength was 735 nm. This fluorescent intensity was two times or more as high as in the case where the excitation wavelength was 780 nm or 690 nm.

From the above results, it was proven that in the infrared fluorescence photography using ICG the use of excitation wavelengths of about 735 nm could provide better excitation efficiency than the use of excitation wavelengths of about 780–805 nm.

Figure 3:
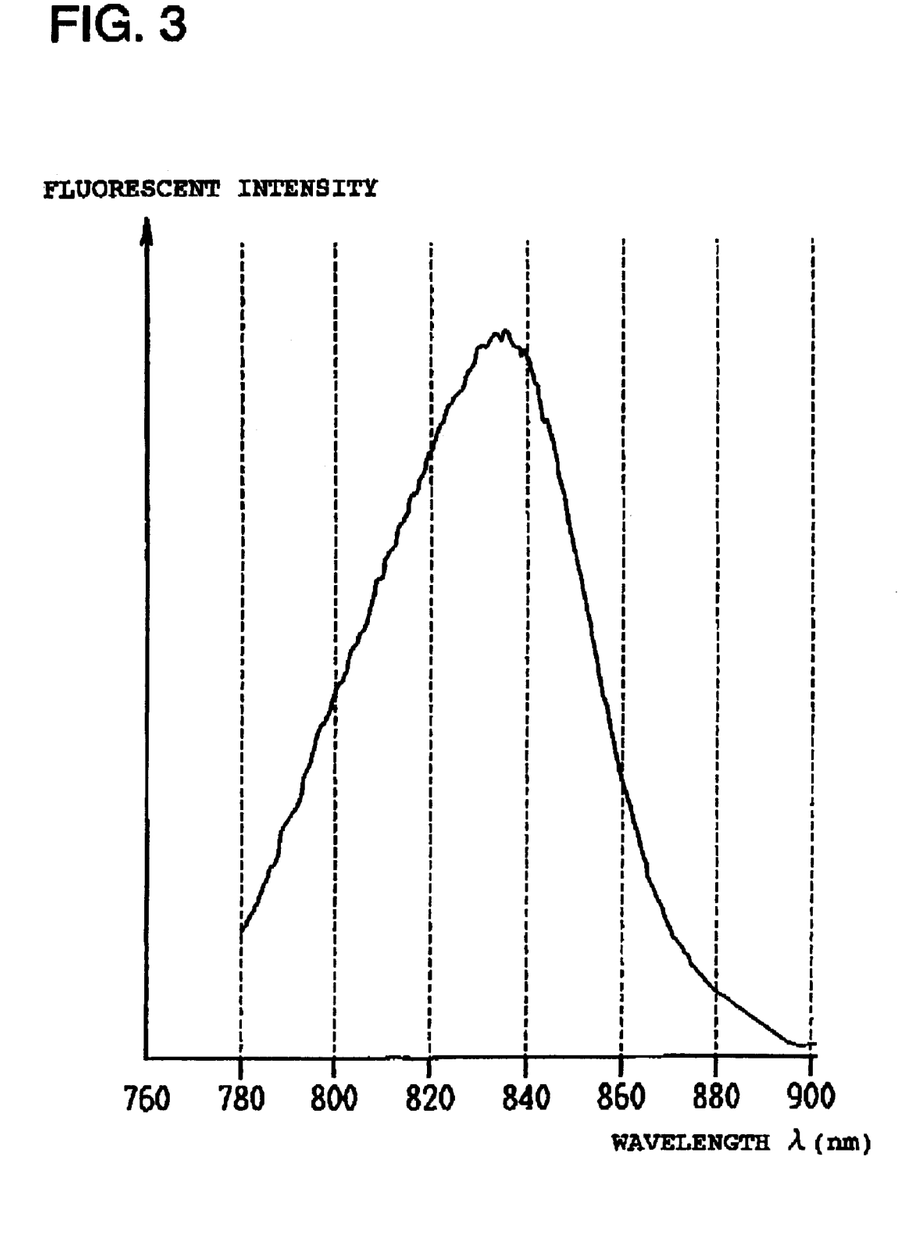
FIG. 3 is a graph showing a fluorescence spectrum obtained by measurements of fluorescent intensity on condition that the exciting light is of a wavelength of about 735 nm.

FIG. 3 is a graph showing a fluorescence spectrum obtained by measurements on the fluorescent intensity of fluorescence emitted from the serum injected with ICG on condition that the excitation wavelength was about 735 nm. As seen from this graph, the fluorescent intensity gradually increased from about 780 nm in a shorter wavelength region than about 800 nm and peaked in a range of about 830 nm to 840 nm. The fluorescent intensity could be measured up to near 900 nm. In this way, since the fluorescent intensity started to increase in the shorter wavelength region than about 800 nm, a photographed image of higher luminance can be more efficiently obtained if the fluorescence photography is carried out with the fluorescence of wavelengths of about 800 nm or more.

Thus, the apparatus for the infrared fluorescence photography using ICG is constructed as follows in order to achieve the fluorescence photography capable of producing photographed images of higher luminance.

Figure 4:
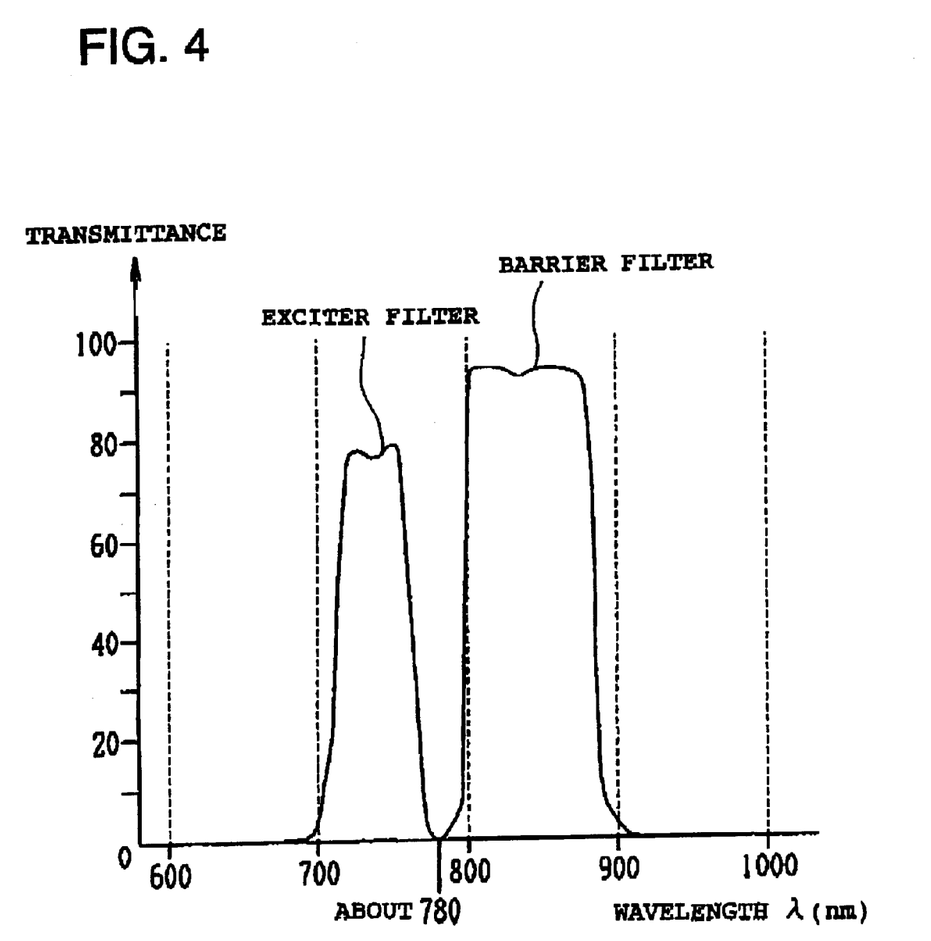
FIG. 4 is a graph schematically showing preferable spectral transmittance properties of an exciter filter and a barrier filter used in an infrared fluorescence photography using ICG.

In a case of using filters, to prevent the influence of false fluorescence by exciting light according to excitation wavelengths, an exciter filter used for giving exciting light is designed to have the property of restricting (transmitting) the wavelengths of the exciting light to about 780 nm or less, as shown in FIG. 4. For instance, the property is determined so that the transmittance is 5% or less for the light of wavelengths of about 700 nm or less, 50% or more (preferably, 70% or more) for the light of wavelengths of about 720–770 nm, and 1% or less for the light of wavelengths of about 780 nm. A barrier filter used for selectively transmitting (filtering) infrared fluorescence is designed to have the property of cutting the light of wavelengths of about 780 nm or less, while transmitting the light of wavelengths of more than about 780 nm. For instance, the property is determined so that the transmittance is 1% or less for the light of wavelengths of about 780 nm or less, 50% or more (preferably, 70% or more) for the light of wavelengths of about 800–860 nm, up to 900 nm in a longer wavelength region as well, and 5% or less for the light of wavelengths of about 930 nm or more.

For the purpose of preventing the influence of false fluorescence, it is preferable that the overlapped region of transmittance wavelengths between the exciter filter and the barrier filter is as small as possible and, preferably, the maximum transmittance in the overlapped region is 0.5% or less. If it is hard to produce filters with so sharp transmittance that the transmittance wavelength regions of both filters are less overlapped, an exciter filter that transmits 50% or more of wavelengths of at least about 720–750 nm is used. Thus, even when the barrier filter is constructed to transmit light of wavelengths including about 800 nm, there is a sufficient margin. This can increase ease of filter construction.

In the case where a laser source which is an efficient light source capable of emitting light of a single wavelength is used as an exciting light source, a laser source capable of emitting near-infrared laser light with the peak wavelength in a range of about 725 nm to 745 nm is used. For instance, a semiconductor laser source (laser diode) may be used. This semiconductor laser source emits a laser beam of a predetermined wavelength region having a slight width, though 10 nm or less in multimode oscillation. In this case, therefore, the barrier filter may further have a margin with respect to a cutting limit in lower wavelengths. For example, the barrier filter may be designed to have the property of cutting most of light with wavelengths of about 760 nm or less, while transmitting light with wavelengths of more than about 760 nm. This filter can transmit most of infrared fluorescence emitted from the fundus (the choroidal veins) while sufficiently preventing the influence of false fluorescence.

Figure 5:
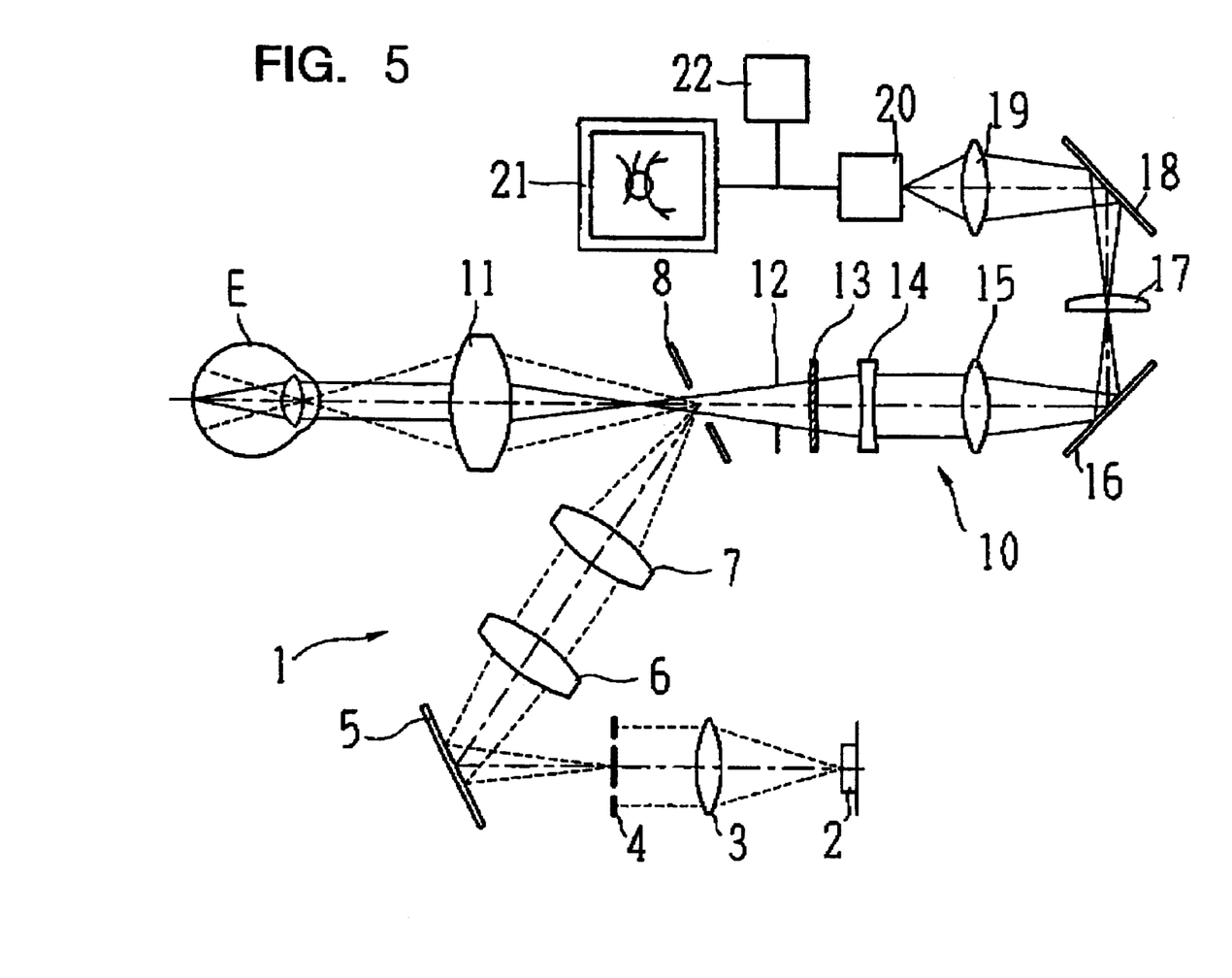
FIG. 5 is a schematic structural view of a fundus photographing device in an embodiment according to the present invention.

Next, explanation is made on a structural example of the fundus photographing device in the present embodiment according to the invention, referring to FIG. 5. Numeral 1 is an illumination optical system constructed of a semiconductor laser source 2 which is an exciting light source, a collimator lens 3, a ring slit plate 4, a mirror 5, relay lenses 6 and 7, and a perforated mirror 8. The semiconductor laser source 2 emits a laser beam of a single wavelength with a peak of about 735 nm.

Numeral 10 is a photographing optical system constructed of an objective lens 11, a photographing stop 12, a barrier filter 13, a focusing lens 14, an imaging lens 15, a mirror 16, a field lens 17, a mirror 18, a relay lens 19, and a CCD camera 20 having the sensitivity to infrared region. The CCD camera 20 is connected to a monitor 21 for displaying a fundus image photographed by the camera 20 and also an image storage section 22 such as a magneto-optic disk and the like.

The barrier filter 13 in the present embodiment has the property of transmitting wavelengths of about 780–900 nm, while cutting wavelengths of less than about 780 nm. Preferably, it has the property of transmitting 50% or more (more preferably, 70% or more) of the wavelengths of about 800–860 nm (see the transmittance property of the barrier filter in FIG. 4). As mentioned above, the exciting light is a laser beam of a single wavelength of about 735 nm. In terms of the lower cutting limit, therefore, the barrier filter 13 may be designed to have the property of cutting light of wavelengths of about 760 nm or less and transmitting more than about 760 nm. This also makes it possible to adequately prevent the influence of false fluorescence.

The infrared exciting light from the semiconductor laser source 2 passes through the collimator lens 3, a ring slit of the plate 4, the mirror 5, the relay lenses 6 and 7, and then is reflected by a reflection plane of the perforated mirror 8 toward the objective lens 11. Thus the exciting light passes through the objective lens 11 and illuminates the fundus of an examinee's eye E.

The fundus in which ICG has been intravenously injected in advance is illuminated with the infrared exciting light emitted from the semiconductor laser source 2. When thus excited, the ICG injected into the choroidal veins emits fluorescence. In the present embodiment, the exciting light used for exciting the ICG is the laser beam having the peak wavelength of about 735 nm. As a result, the ICG emits the fluorescence of higher luminance than in the case where the exciting light having the peak wavelength in the range of about 780 nm to 800 nm is used. Since the laser beam of a single wavelength is used as the exciting light, excitation efficiency can be enhanced by illumination of a low light amount as compared with the case where an exciter filter is used.

The fluorescence emitted from the fundus (the choroidal veins) passes through the objective lens 11, an aperture of the perforated mirror 8, the photographing stop 12, the barrier filter 13, the focusing lens 14, the imaging lens 15, the mirror 16, the field lens 17, the mirror 18, and the relay lens 19, and then is focused on the CCD camera 20 to form a fundus image. The barrier filter 13 allows filtering (transmitting) of the fluorescence of not only the peak wavelengths of 830–840 nm but also shorter wavelengths than about 800 nm (about 780–800 nm) which is a rising edge for the peak, whereby faint infrared fluorescence can be easily captured. The barrier filter 13 sufficiently cuts the wavelengths of the exciting light, thus enabling prevention of the influence of false fluorescence. The fundus image photographed by the CCD camera 20 is displayed in the monitor 21. The photographed image is properly stored in the image storage section 22.

By the use of the laser beam of wavelengths efficient for excitation and the use of the above structured barrier filter, even the fluorescence of very low luminance of the early stage of ICG injection as compared with the conventional case can be captured by the CCD camera 20. This makes it possible to provide more detailed information for diagnosis of choroidal circulation. The intensity of the whole fluorescence emitted from the fundus increases, so that the choroidal circulation dynamics from the early to the late stage of ICG injection can be obtained as As means for filtering infrared fluorescence for photography, there may be arranged the barrier filter 13 in the optical path of the photographing optical system or the CCD camera 20. Alternatively, a prism and the like may be used to separate the infrared fluorescence, which is then introduced as photographing luminous flux.

Figure 6:
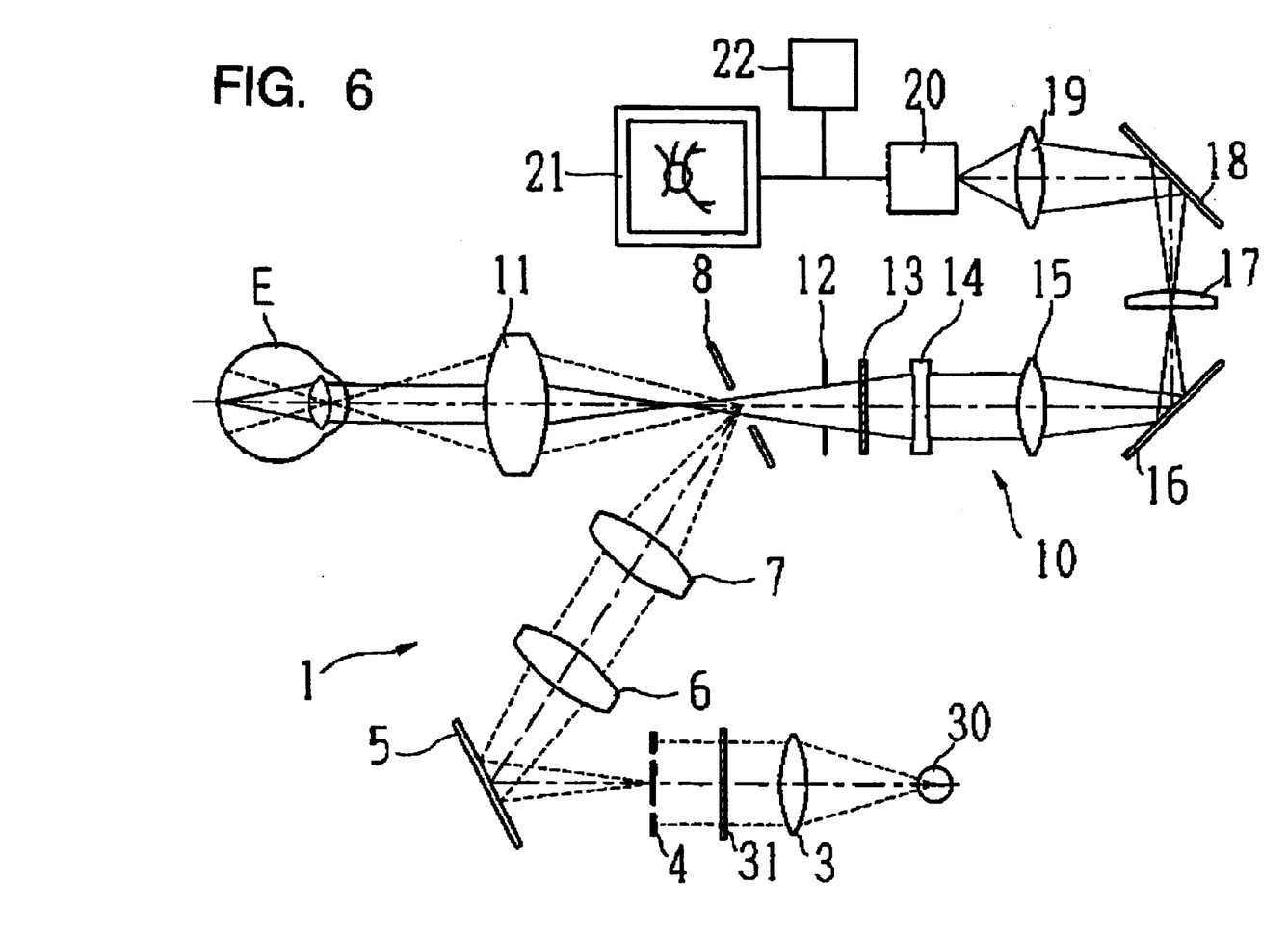
FIG. 6 is a schematic structural view of a fundus photographing device in another example.

In the above embodiment, the laser beam of a single wavelength is used as the exciting light. An alternative design is, as shown in FIG. 6, the us of a light source 30 such as a xenon lamp and an exciter filter 31 to restrict (transmit) excitation wavelengths. In this case, the exciter filter 31 and the barrier filter 13 have the wavelength properties of the filter structure mentioned above (see FIG. 4).

By the use of the exciter filter 31 and the barrier filter 13 with the above properties, like the above embodiment, fluorescence of higher luminance than in the conventional case can be obtained while preventing the influence of false fluorescence. In the case where the exciter filter 31 is designed to transmit light of wavelengths restricted to about 720–750 nm, it can prevent the influence of false fluorescence with sufficient margin even if the barrier filter 13 is designed to allow the transmittance to wavelengths including about 800 nm. Thus, manufacture of the two filters can be facilitated.

As mentioned above, the fundus photographing device according to the invention enables infrared fluorescence photography of high luminance while preventing the influence of false fluorescence. Accordingly, the fluorescence can be captured at the early stage of injection of the fluorescent agent into the choroidal veins, thereby enabling more detailed diagnosis of choroidal circulation dynamics.

The foregoing description of the preferred embodiment of the invention has been presented for purposes of illustration and description. It is not intended to be exhaustive or to limit the invention to the precise for disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto.

What is claimed is:

1. A fundus photographing device for conducting infrared fluorescence photography on a fundus of an examinee's eye after intravenously injecting a fluorescent agent, the fluorescent agent having a peak absorption wavelength region and emitting infrared fluorescence by exciting, the device including:

an illumination optical system for illuminating the fundus with exciting light having a main wavelength shorter than the peak absorption wavelength region, thereby exciting the injected fluorescent agent, an amount of the emitted infrared fluorescence by the exciting light having the main wavelength shorter than the peak absorption wavelength region being larger than an amount of emitted infrared fluorescence by exciting light having a main wavelength within the peak absorption wavelength region; and a photographing optical system including filtering means for transmitting the infrared fluorescence emitted from the injected fluorescent agent and intercepting most of the reflected exciting light, and a photographing element for photographing an image of the fundus with the infrared fluorescence transmitted through the filtering means.

2. The fundus photographing device according to claim 1, wherein the filtering means includes a barrier filter disposed in the photographing optical system, and the barrier filter has a property of transmitting the infrared fluorescence emitted from the injected fluorescent agent and intercepting most of the reflected exciting light.

3. The fundus photographing device according to claim 2, wherein the fluorescent agent includes indocyanine green (ICG), wherein the illumination optical system includes a laser source for emitting a laser beam used as the exciting light, the laser beam having the main wavelength within the range of approximately 725 nm to 745 nm, wherein the barrier filter has a property of intercepting most of light in the wavelength region of approximately 760 nm or less.

4. The fundus photographing device according to claim 3, wherein the barrier filter has a property of transmitting approximately 50% or more of light in the wavelength region of approximately 800 nm to 860 nm.

5. The fundus photographing device according to claim 2, wherein the fluorescent agent includes indocyanine green (ICG), wherein the illumination optical system includes an illumination light source for emitting illumination light used as the exciting light and an exciter filter having a property of transmitting approximately 50% or more of the illumination light in the wavelength region of approximately 720 nm to 770 nm, and transmitting approximately 1% or less of the illumination light in the wavelength region of approximately 680 nm or more.

6. The fundus photographing device according to claim 5, wherein the barrier filter has a property of transmitting approximately 50% or more of light in the wavelength region of approximately 800 nm to 860 nm.

7. The fundus photographing device according to claim 5, wherein the illumination light source includes a commonly used illumination light source including a xenon lamp.

* * * * *